United States Patent [19]

Inoue et al.

[11] Patent Number: 4,981,800
[45] Date of Patent: Jan. 1, 1991

[54] METHOD FOR CULTURING MICROORGANISM

[75] Inventors: Akira Inoue; Kouki Horikoshi, both of Tokyo, Japan

[73] Assignee: Research Development Corporation of Japan, Tokyo, Japan

[21] Appl. No.: 174,958

[22] Filed: Mar. 29, 1988

[30] Foreign Application Priority Data

Mar. 30, 1987 [JP] Japan ................................. 62-74500

[51] Int. Cl.$^5$ .................. C12R 1/185; C12R 1/38; C12R 1/40; C12N 1/26
[52] U.S. Cl. .................................. 435/248; 435/247; 435/249; 435/250; 435/252.8; 435/253.3
[58] Field of Search ............... 435/247, 248, 249, 250, 435/252.8, 253.3

[56] References Cited

U.S. PATENT DOCUMENTS

Re. 30,543  3/1981  Hitzman et al. .................... 435/247
3,326,770  6/1967  Coty ..................................... 435/248

FOREIGN PATENT DOCUMENTS 0161511  11/1985  European Pat. Off. ......... 435/253.3

50-154480  12/1975  Japan ................................. 435/247

OTHER PUBLICATIONS

Patel et al., "Amino Acid Production by Submerged Cultivation of *Pseudomonas fluorescens* on Gasoline," Folia Microbiol. 30, 420–426, (1985).

Higashihara et al., "Production of 1-Phenazinecarboxylic Acid from Ethanol by a Hydrocarbon–Assimilating Bacterium, *Pseudomonas aeruginosa*", Rep. Ferment. Res. Inst. (Yatabe) 0(63): 81–94, 1985, (Sec. BA 80(9):76248).

*Primary Examiner*—Herbert J. Lilling
*Attorney, Agent, or Firm*—Nixon & Vanderhye

[57] ABSTRACT

A method for culturing microorganisms belonging to the genus Pseudomonas or the genus Escherichia and having tolerance to an organic solvent such as any one of hydrocarbons, alcohols, ethers, ketones and their derivatives or their mixture in a medium containing the organic solvent in a concentration of 0.3% or more. The present method can be widely utilized in the fields of bioreactor, liquid-waste treatment, protein engineering, etc.

4 Claims, No Drawings

METHOD FOR CULTURING MICROORGANISM

BACKGROUND OF THE INVENTION

This invention relates to a method for culturing a microorganism having a tolerance to an organic solvent. In further detail, this invention relates to a method for culturing a microorganism having a tolerance to an organic solvent selected from among hydrocarbons, alcohols, ethers, ketones, their derivatives and their mixtures.

As conventional examples of culturing a microorganism in a medium containing hydrocarbons or their derivatives, there are such many reports as of the growing of Nocardia sp. in a medium containing hexane or hexadecane [R. L. Raymond, *Appl. Microbiol.*, vol. 15, pp. 857~865 (1967)], the growing of Bacterium JOB5 in a medium containing cyclopentane or cyclohexane [J. Ooyama and J. W. Foster, *Antonie von Leenwenlook*, vol. 31, pp. 45~65 (965)], the growing of Fseudomonas sp., Achromobacter sp., and Nocardia sp. in a medium containing benzene, ethyl benzene, toluene or xylene [D. Cleus and N. Walkes, *J. Gen. Microbiol*, vol. 36, pp. 107~122 (1964)], etc. can be enumerated. However, these microorganisms are cultured by bringing the same into contact with hydrocarbons which are concentrated low or in the form of steam in any case owing to the fact that hydrocarbons generally show toxicity to microorganisms. That is, when the fermentation is carried out by using these hydrocarbons as substrates, it is carried out by supplying these compounds in the form of steam so that the compounds are not brought into contact with microorganisms directly or by maintaining these compounds in low concentration (0.2or less) at which a toxic effect is not shown. Consequently, in the fermentation using hydrocarbons as substrates, there are problems not only of low productivity but also of operation because of the difficulty in controlling the substrates to low concentration. Furthermore, in case of using a lightly water-soluble substance, there is a disadvantage that the productivitY becomes low in &he microbial reaction going to the low solubility of the substance.

SUMMARY OF THE INVENTION

In order to solve the foregoing problems, the present inventors have made an extensive search so as to obtain a microorganism which can grow up in a medium containing a solvent such as hYdrocarbon or the like in a high concentration, that is, a microorganism having a tolerance to a solvent such as hydrocarbon or the like. As a result, the prevent inventors found out microorganisms having the aforementioned tolerance and have completed the invention of a method for culturing these microorganisms in a medium containing a solvent.

That is, the object of the present invention lies in providing a method for culturing a microorganism having a tolerance to an organic solvent.

Because microorganisms belonging to the genus Pseudomonas or the genus Escherichia in the present invention have excellent tolerance to a solvent containing hydrocarbons, alcohols, ethers, ketones and their derivatives or their mixtures which are commonly used, said microorganisms can be prevented from the saprophyte coniamination by culturing the same in the presence of the above solvents. In this case, because the heat killing is not required, it becomes possible to use thermolabile additives. In case of carrying out the culture by using these solvents as substrates, the substrates can be supplied at high concentrations. Thus, the improvement in productivity can be expected. In addition, in case that the substrate concentration is high as described above, the control over the addition of the substrate becomes easier. In case of toxic substances to be used for the culture by dissolving in these solvents, the concentration control also becomes possible. Similarly, in case of slightly water soluble substances &o be used also by dissolving in the solvents, they can be used at high concentrations. Because of the excellent effects as above, the present method for culturing a microorganisms can be utilized widely in the fields of bioreactor, liquid-waste treatment, protein engineering, etc.

DETAILED DESCRIPTION OF THE INVENTION

A method for culturing a microorganism according to the present invention is characterized by culturing a microorganism belonging to the genus Pseudomonas or the genus Escherichia and having a tolerance to an organic solvent in a medium containing 0.3% or more organic solvent.

As a microorganism belonging &o the genus Pseudomonas, Pseudomonas aeruminosa, pseudomonas fluorescens, *Pseudomonas putida*, Pseudomonas sp. STM-801, Pseudomonas sp. STM 904 can be enumerated. As a microorganism belonging to the genus Escherichia, *Escherichia coli* can be enumerated.

As an organic solvent to which these microorganisms show tolerance, any one of aliphatic hydrocarbons, alicyclic hydrocarbons, aromatic hydrocarbons, alcohols, ethers, ketones and their derivatives or their mixture can be enumerated.

The microorganisms belonging to the genus Pseudomonas or the genus Escherichia can grow in a medium containing aliphatic hydrocarbons, alicyclic hydrocarbons, alcohols, ethers, ketones, aromatic hydrocarbons which are particularly highly toxic and their derivatives in a concentration as high as 0.3% or more. In addition, these strains can grow even in a medium containing the above compounds in a concentration as high as 50% or more. Thus, in the culture of these microorganisms, a substrate can be supplied in large quantities, Whereby &he improvement of productivity and the control over the substrate concentration become easier and the prevention of the saprophyte contamination becomes possible. Furthermore, the improvement of productivity in the microbial reaction and the control over the concentration of toxic substances become possible by dissolving slightly water soluble substances in various hydrocarbon.

The strains belonging to the genus Pseudomonas, i.e., STM-603, STM-801 and STM 904 were obtained by culturing soil which the present inventors collected from all over the country in media containing 0.1 % glucose, 0.25% yeast extract, 0.5 % peptone and 50% solvent (aliphatic hydrocarbons. alicyclic hydrocarbons, aromatic hYdrocarbons, alcohols, ethers and ketones) and then isolating colonies formed.

As specific examples of solvents, pentane, hexane, heptane, octane, isooctane, nonane decane, 1- or 2-hexene, 1-octene, 1-dodecene, 1,3-pentadiene, 1,5-hexadiene, 1,7-octadiene, etc. as aliphatic hydrocarbons; cyclopentane, cyclohexane, methyl cyclopentane, methyl cyclohexane, etc. as alicyclic hydrocarbons; toluene, xylene, styrene, ethyl benzene, chlorobenzene. etc. as aroma&ic hydrocarbons; 1-heptanol, 1-octanol, 1- decanol, etc. as alcohols; n-hexyl ether, n-butyl phenyl ether, diphenyl ether, dibenzyl ether, methoxytoluene, etc. as ethers; and 2-pentanone, 2-hexanone, 2-heptanone, cyclohexanone, etc. as kentones can be enumerated.

These strains, STM-603, STM-801 and STM-904 have the following bacteriological properties respectively:

ever, *Pseudomonas putida* is intolerant to hydrocarbons. The tolerance of IFO 3738 is a standard strain of *Pseudomonas putida* and the present strain STM-603 to various solvents were examined. The results were given in Table 2.

TABLE 1
Morphological and Physiological Properties of Isoltes STM-603, STM-801 and STM-904

|  | STM-603 | STM-801 | STM-904 |
|---|---|---|---|
| A. Morphological Properties (24-hr. culture in a bouillon liquid medium) | | | |
| a. Shape and Size of Cell | rod 0.7~1.0 μm × 2~4 μm | rod 0.7~1.0 μm × 2~15 μm | rod 0.7~1.0 μm × 3~15 μm |
| b. Polymorphism of Cell | − | + or − | + or − |
| c. Motility | − | − | − |
| d. Sporulation | − | − | − |
| d. Gram's Stain | − | − | − |
| B. Growth on various media (24-hr. culture at 30° C.) | | | |
| a. Bouillon agar plate culture | Circular colonies of 0.5 to 1 mm with lustrously flesh-colored surface | Circular colonies of 0.5 to 1 mm with lustrously flesh-colored surface | Circular colonies of 0.5 to 1 mm with lustrously flesh-colored surface |
| b. Bouillon agar slant culture | Grown on the surface of the medium | Grown on the surface of the medium | Grown on the surface of the medium |
| c. Bouillon liquid medium | Grown | Grown | Grown |
| d. Bouillon gelatin stab culture | No gelatin liquefaction | No gelatin liquefaction | No gelatin liquefaction |
| C. Physiological Properties | | | |
| a. Nitrate reduction | − | − | − |
| b. Starch hydrolysis | − | − | − |
| c. Poly-β-hydroxybutyrate hydrolysis | − | − | − |
| d. Tween 80 hydrolysis | − | − | − |
| e. Arginine hydrolysis | + | + | + |
| f. Pigment formation (King B medium) | Yellowish green, water-soluble fluorochrome | Yellowish green, water-soluble fluorochrome | Not formed |
| g. Oxidase | + | + | + |
| h. Catalase | + | + | + |
| i. Growth range | | | |
| pH | 5.0~9.5 | 5.0~9.5 | 5.0~9.5 |
| Temperature | Not grown at 41° C. | Not grown at 41° C. | Not grown at 41° C. |
| j. Behavior toward oxygen | Aerobic | Aerobic | Aerobic |
| k. O-F test | Oxidative | Oxidative | Oxidative |
| l. Citrate utilization | + | + | + |
| m. Levan production from sucrose | − | − | − |
| n. DNAse production | − | − | − |
| o. Acylamidase production | − | − | − |
| p. Assimilation: | | | |
| D-glucose | + | + | + |
| D-fructose | + | + | + |
| D-oxylose | + | + | + |
| D-maltose | − | − | − |
| Sucrose | − | − | − |
| Lactose | − | − | − |
| D-trehalose | − | − | − |
| Mannitol | − | − | − |
| 2-ketogluconic acid | + | + | + |
| L-valine | + | + | + |
| β-alanine | + | + | + |
| DL-arginine | + | + | + |
| Acetoamido | − | − | − |
| Meso-inositol | − | − | − |
| Benzyl amine | + | + | + |
| Geraniol | − | − | − |

On the basis of the bacteriological properties given in Table 1, the screening of each strain was carried out according to *Bergey's Manual of Determinative Bacteriology*, (8th ed., 1975) was carried out. As a result, the bateriological properties of the strain STM-603 were compatible with those of *Pseudomonas putida*. How-

TABLE 2

| Solvent | *Pseudomonas putida* IFO 3738 | STM-603 |
|---|---|---|
| Toluene | − | + |
| P-xylene | − | + |
| Styrene | − | + |

From these facts that the strain STM-603 and *Pseudomonas putida* had morphological, physiological and bateriological properties in common but differed from one another in the behavior toward the solvent tolerance, the strain STM-603 were recognized as a new strain belonging to *Pseudo-monas putida* and designated as *Pseudomonas putida* var. STM-603.

Regarding strains STM-801 and STM-904, *Pseudomonas putida* can be enumerated as their similar known strain. Thus, the present inventors have made a further detailed comparison between the present strains STM-801 and STM-904 and IFO 3738 as a standard strain of *Pseudomonas putida* with respect to their bacteriological properties, thereby obtaining the following results, as Will be also given in Table 3:

(1) The cell size of *Pseudomonas putida* is 0.7 to 0.7 to 1.0μ by 2 to 4μ, while that of STM-801 and STM 904 are respectively 0.7 to 1.0μ by 2 to 15μ and 0.7 to 1.0μ by 3 to 15μ. That is, the size of the present strains is 3 to 4 times that of *Pseudomonas putida*.

(2) Regarding the motility, all the cells show the motility in case of *Pseudomonas putida*. However, in case of STM-801 and STM-904, some cells show the motility, but others do not.

(3) Regarding the pigment formation, yellowish green water-soluble fluorochrome is formed in case of *Pseudomonas putida*. However, in case of STM-801 and STM-904, the former forms the same pigment as above, but the latter does not.

(4) Regarding the solvent tolerance with respect to toluene, p-xylene and styrene, *Pseudomonas putida* does not show a tolerance at all while STM-801 and STM-904 show tolerance.

From these results, it is recognized that the strains STM 801 and STM-904 correspond to new species because they are obviously different from *Pseudomonas putida* and because there is no known species corresponding to these strains. So, the present inventors designated the straina STM-801 and STM 904 as Pseudomonas sp. STM-801 and Pseudomonas sp. STM-904 respectively.

strains, *Pseudomonas aeruginosa* IFO 3924, *Pseudomonas fluorescens* IFO-3507, *Pseudomonas putida* IFO-3738, etc. can be enumerated, and as the present microorganism belonging to the genus Escherichia, *Escherichia coli* IFO-3806 can be enumerated.

As a medium for culturing these strains, an ordinary medium containing a carbon source, a nitrogen source, an inorganic ion, etc. is used.

As a carbon source, any of &hose which can be assimilated, for example, sugars such as glucose, fructose, xylose, starch hydrolysate, etc., hYdrocarbons such as toluene, p-xylene, etc., alcohols such as methanol, ethanol, etc., etc. can be used. As a nitrogen source, yeast extract, dry yeast, peptonic, meat extract, corn steep liquor, casamino acid, ammonium chloride, ammonium sulfate, urea, sodium nitrate, etc. are used. As an inorganic ion, phosphoric acid ion, magnesium ion, iron ion, calcium ion, potassium ion, copper ion, manganese ion, etc. are used.

As a solvent, any on®of aliphatic hYdrocarbons, alicyclic hydrocarbons, aromatic hydrocarbons, alcohols, ethers, ketones and their derivatives or &heir mixture can be used. As specific examples of these solvents, pentane, hexane, heptane, octane, isooctane, nonane, decane, 1- or 2- hexene, 1-idene, 1-dodecene, 1,3-pentadiene, i,5-hexadiene, 1,7 octadiene, etc. as aliphatic hydrocarbons; cyclopentane, cyclohexane, methyl cyclopentane, methyl cyclohexane, etc. as alicyclic hydrocarbons; toluene, xylene, styrene, ethyl benzene, chlorobenzene, etc. as aromatic hydrocarbons; 1-heptanol, 1-octanol, 1 decanol, etc. as alcohols; n-hexyl ether, in butyl phenyl ether, diphenyl ether, dibenzyl ether, methoxytoluene, etc. as ethers; and 2 pentanone, 2-hexanone, 2-heptanone, cyclohexanone, etc. as kentones can be enumerated. The contents of these solvent in a medium is 0.3% or more. Said solvents may be either contained in a medium previously or add®d to a medium afterwards.

The culture is carried out at pH 5 to 9 at 20 to 40° C. under aerobic conditions.

TABLE 3

|  | *Pseudomonas putida* IFO 3738 | STM-801 | STM-904 |
|---|---|---|---|
| (1) Size of Cell | 0.7~1.0 × 2~4μ | 0.7~1.0 × 2~15μ | 0.7~1.0 × 3~15μ |
| (2) Motility | + | + or − | + or − |
| (3) Pigment Formation | Yellowish green, water-soluble fluorochrome | Yellowish green, water-soluble fluorochrome | Not formed |
| (4) Solvent Tolerance: |  |  |  |
| Toluene | − | + | + |
| P-xylene | − | + | + |
| Styrene | − | + | + |

Said *Pseudomonas putida* var. STM-603, pseudomonas sp. STM-801 and Pseudomonas sp. STM-04 were deposited in Fermentation Research Institute of Agency of Industrial Science and Technology respectively with the accession numbers FERM BP-1751 (Bikoken-kinki No. 9228), FERM BP-1749 (Bikoken-klnki No. 9226) and FERM BP-1750 (Bikoken-kinki No. 9227).

As the present microorganisms belonging to the genus Pseudomonas other than the aforementioned

TEST EXAMPLE 1

*Pseudomonas putida* var. STM-603, Pseudomonas sp. STM-80I, Pseudomonas sp. STM-904 and various known strains were respectively inoculated into media (pH 7.0) respectively containing 1.0g/1 of glucose, 2.5g/1 of yeast extract and 5.0g/1 of peptone. Then, each 5ml of solvents given in Table 4 was added to each 5ml of said media. After culturing the resulting media at 37° for 48 hours, the growth of each strain was compared. The results were given in Table 4.

TABLE 4

Comparison of Solvent Tolerance of Various Strains

| Strain | Cyclohexane | Toluene | P-xylene | Styrene |
|---|---|---|---|---|
| *Pseudomonas putida* var. STM-603 | + | + | + | + |
| Pseudomonas sp. STM-801 | + | + | + | + |
| Pseudomonas sp. STM-904 | + | + | + | + |
| *Pseudomonas fluorescens* IFO-3507 | − | − | − | − |
| *Pseudomonas pseudoalcaligenes* ATCC-12815 | − | − | − | − |
| *Arthrobacter globiformus* IFO-3062 | − | − | − | − |
| *Agrobacterium tumefaciens* IFO-3058 | − | − | − | − |
| *Escherichia coli* IFO-3806 | − | − | − | − |
| *Bacillus cereus* IFO-3131 | − | − | − | − |
| *Bacillus coagulans* IFO-3557 | − | − | − | − |

−: Not grown
+: Grown (O.D$_{660}$ > 0.50)

EXAMPLE 1

A medium prepared by adding 1.0l of distilled water to 1.0g of glucose, 2.5g of yeast extract and 5.0g of peptone and adjusted to pH 7.2 was dispensed in 100ml portions into 500-ml ribbed conical flasks, in which *Pseudomonas putida* var. STM-603 was inoculated without sterilizing said flasks. After adding each 30ml of toluene to the flasks, the culture was carried out at 37° C. for 48 hours. As a result, 1.2mg/ml of Pseudomonas putida var. STM 603 cell mass was obtained, where the contamination and the growth of other microorganisms were not observed.

EXAMPLE 2

A medium prepared by adding 1.0l of distilled water to 1.0 g of glucose, 2.5g of yeast extract and 5.0g of peptone and adjusted to pH 7.2 was dispensed in 100ml portions into 500-ml ribbed conical flasks, in which Pseudomonas sp. STM-801 was inoculated without sterilizing said flasks. After adding each 30ml of toluene to the flasks, the culture was carried out at 37° C. for 48 hours. As a result, 1.1mg/ml of Pseudomonas sp. STM 801 cell mass was obtained, where the contamination and the growth of other microorganisms were not observed.

EXAMPLE 3

Strains of the genus Pseudomonas were inoculated in each 5ml of sterile bouillon liquid medium (containing 5.0g of meat extract, 15.0g of peptone, 5.0g of sodium chloride, 5.0g of dibasic potassium phosphate and 1l of distilled water; pH 7.0), and a strain of the genus Escherichia was inoculated in 5ml of sterile LB liquid medium (containing 10g of tryptone, 5g of yeast extract, 10g of sodium chloride, 1g of glucose and 1l of distilled water; pH 7). Then, each 5ml solvents given in Table 5 was added to each medium. The culture was carried out at 30° C. for 48 hours. The state of the growth of each strain was given in Table 5. The growth was monitored by measuring turbidity (wave length: 660nm, a colorimeter "Spectronic 21" manufactured by Bausch & Lomb Corp.).

TABLE 5

| Strain | Solvent | |
|---|---|---|
| | hexane | cyclohexane |
| *Pseudomonas aeruginosa* IFO 3924 | − | + |
| *Pseudomonas fluorescens* IFO 3507 | + | − |
| *Pseudomonas putida* IFO 3738 | + | + |
| *Escherichia coli* IFO 3806 | + | − |

−: Not grown
+: Grown (O.D$_{660}$ > 0.50)

EXAMPLE 4

The same medium as that of Example 1 was prepared, dispensed in 5ml portions into large test tubes and steam-sterilized at 121° C. for 15 minutes. Then, *Pseudomonas putida* var. STM-603, Pseudomonas sp. STM-801 and Pseudomonas sp. STM-904 were respectively inoculated in the large test tubes, to which each 5m( of various solvents given in Table 6 was added. The culture was carried out at 48 hours using a test tube shaker. The state of growth after 48 hours was given in Table 6. The growth was monitored by measuring turbidity (wave length: 660nm, a colorimeter "Spectronic 21" manufactured by Bausch & Lomb Corp.).

TABLE 6

Tolerance of *Pseudomonas putida* var. STM-603, Pseudomonas sp. STM-801 and Pseudomonas sp. STM-904 to Various Solvents

| Solvent | Strain | | |
|---|---|---|---|
| | STM-603 | STM-801 | STM-904 |
| Aliphatic hydrocarbons: | | | |
| pentane | + | + | + |
| hexane | + | + | + |
| heptane | + | + | + |
| octane | + | + | + |
| isooctane | + | + | + |
| nonane | + | + | + |
| decane | + | + | + |
| 1- or 2-hexene | + | + | + |
| 1-octene | + | + | + |
| 1 dodecene | + | + | + |
| 1,3-pentadiene | ± | ± | ± |
| 1,5-hexadiene | + | + | + |
| 1,7-octadiene | + | + | + |
| Alicyclic hydrocarbons: | | | |
| cyclopentane | + | + | + |
| methyl cyclopentane | + | + | + |
| cyclohexane | + | + | + |
| methyl cyclohexane | + | + | + |
| butyl cyclohexane | + | + | + |

TABLE 6-continued

Tolerance of *Pseudomonas putida* var. STM-603, Pseudomonas sp. STM-801 and Pseudomonas sp. STM-904 to Various Solvents

| Solvent | Strain | | |
|---|---|---|---|
| | STM-603 | STM-801 | STM-904 |
| cyclooctane | + | + | + |
| Aromatic hydrocarbons: | | | |
| toluene | + | + | + |
| p-xylene | + | + | + |
| o-,m-p-xylene | + | + | + |
| chlorobenzene | + | + | + |
| o-dichlorobenzene | + | + | + |
| 1,2,4-trichlorobenzene | + | + | + |
| bromobenzene | + | + | + |
| ethyl benzene | + | + | + |
| propyl benzene | + | + | + |
| styrene | + | + | + |
| Alcohols: | | | |
| 1-heptanol | + | + | + |
| 1-octanol | + | + | + |
| 1-decanol | + | + | + |
| Ethers: | | | |
| n-hexyl ether | + | + | + |
| n-butyl phenyl ether | + | + | + |
| diphenyl ether | + | + | + |
| dibenzyl ether | + | + | + |
| methoxytoluene | + | + | + |

±: Grown ($0 < O.D_{660} < 0.50$)
+: Grown ($O.D_{660} > 0.50$)

EXAMPLE 5

The same medium as that of Example 1 was prepared, dispensed in 5ml portions into large test tubes and steam-sterilized at 121° for 15 minutes. Then, *Pseudomonas putida* STM-603, Pseudomonas sp. STM-801 and Pseudomonas sp. STM-904 were respectively inoculated in the test tubes, to each of which 0.25ml of various solvents given in Table 7 was added. The culture was carried out at 37° using a test tube shaker. The state of growth after 48 hours was given in Table 7. The growth was monitored by measuring turbidity (wave length: 660nm, a colorimeter "Spectronic 21" manufactured by Bausch & Lomb Corp.).

TABLE 7

| Solvent | Strain | | |
|---|---|---|---|
| Ketones | STM-603 | STM-801 | STM-904 |
| 2-pentanone | ± | ± | ± |
| 2-hexanone | ± | ± | ± |
| 2-heptanone | + | + | + |
| cyclohexanone | ± | ± | ± |

—: Not grown
±: Grown ($0 < O.D_{660} < 0.50$)
+: Grown ($O.D_{660} > 0.50$)

What is claimed is:

1. A method for culturing a microorganism which comprises culturing a microorganism having a tolerance to an organic solvent in a medium containing at least 23 vol/vol% of said organic solvent, said microorganism being selected from the group consisting of *Pseudomonas putide* var. STM-603, Pseudomonas sp. STM-801 and Pseudomonas sp. STM-904 and said organic solvent being selected from the group consisting of $C_5$–$C_{10}$ alkanes; $C_6$–$C_{12}$ alkenes; $C_5$–$C_8$ alkadienes; $C_5$–$C_8$ alicyclic hydrocarbons; $C_5$–$C_8$ alicyclic hydrocarbons containing a lower alkyl substituent; aromatic hydrocarbons having from one to three substituents thereon selected from the group consisting of lower alkyl, halogen and lower alkenyl; $C_7$–$C_{10}$ aliphatic alcohols; and ethers.

2. A method according to claim 1, wherein the microorganism is *Pseudomonas putida* var. STM-603.

3. A method according to claim 1, wherein the microorganism is Pseudomonas sp. STM-801.

4. A method according to claim 1, wherein the microorganism is Pseudomonas sp. STM-904.

* * * * *